United States Patent
Hooper et al.

(10) Patent No.: US 9,498,569 B2
(45) Date of Patent: *Nov. 22, 2016

(54) SYRINGE DEVICE, SYSTEM AND METHOD FOR DELIVERING OZONE GAS

(71) Applicant: Minimus Spine, Inc., Austin, TX (US)

(72) Inventors: David M. Hooper, Austin, TX (US); Thomas Foster, Salem, MA (US); Noel Henson, Austin, TX (US)

(73) Assignee: Minimus Spine, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/597,906

(22) Filed: Jan. 15, 2015

(65) Prior Publication Data

US 2015/0133852 A1 May 14, 2015

Related U.S. Application Data

(62) Division of application No. 12/000,374, filed on Dec. 12, 2007, now Pat. No. 8,961,471.

(51) Int. Cl.
*A61M 5/00* (2006.01)
*A61M 5/31* (2006.01)
(Continued)

(52) U.S. Cl.
CPC ............ *A61M 5/002* (2013.01); *A61M 5/001* (2013.01); *A61M 5/3129* (2013.01); *A61M 39/16* (2013.01);
(Continued)

(58) Field of Classification Search
CPC ............... A61M 2005/006; A61M 2202/0216; A61M 5/001; A61M 5/002; A61M
(Continued)

(56) References Cited

U.S. PATENT DOCUMENTS 4,725,412 A 2/1988 Ito
4,968,302 A 11/1990 Schluter et al.
(Continued)

FOREIGN PATENT DOCUMENTS

CN 1822875 A 8/2006
DE 447 936 7/1927
(Continued)

OTHER PUBLICATIONS

Canadian Office Action dated Jan. 26, 2015, for corresponding CA Application No. 2,708,301, 3 pages.
(Continued)

*Primary Examiner* — Kevin C Sirmons
*Assistant Examiner* — Shefali Patel
(74) *Attorney, Agent, or Firm* — Maier & Maier, PLLC (57) ABSTRACT

In accordance with at least one exemplary embodiment, a syringe device, a method and a system for delivering a therapeutic amount of ozone are disclosed. A sterility case can enclose a syringe portion and can maintain sterility while the syringe device is interfaced to an ozone generator. A valvably-controlled fluid channel can extend from a barrel of the syringe portion through the case. Conducting elements can be attached to the case and can breach the case. The conducting elements can be connected to electrodes. The electrodes can be attached to the syringe portion. The syringe portion can be filled with oxygen gas via the valvably-controlled fluid channel. An electric current can be provided to the conducting elements from the ozone generator resulting in a corona discharge from at least one of the electrodes. A therapeutic amount of ozone gas can be produced from the oxygen gas and the syringe portion delivered into a sterile field without compromise.

3 Claims, 8 Drawing Sheets

(51) Int. Cl.
*A61M 39/16* (2006.01)
*C01B 13/11* (2006.01)

(52) U.S. Cl.
CPC . *A61M 2005/006* (2013.01); *A61M 2005/3117* (2013.01); *A61M 2039/167* (2013.01); *A61M 2202/0216* (2013.01); *A61M 2205/7536* (2013.01); *A61M 2209/06* (2013.01); *C01B 13/11* (2013.01); *C01B 2201/64* (2013.01)

(58) Field of Classification Search
CPC .................... 2005/3117;A61M 5/3129; A61M 2209/06
See application file for complete search history.

(56) References Cited

U.S. PATENT DOCUMENTS

| | | | |
|---|---|---|---|
| 5,052,382 A | 10/1991 | Wainwright | |
| 5,084,021 A | 1/1992 | Baldwin | |
| 5,284,570 A * | 2/1994 | Savage | A61B 5/1405 204/403.02 |
| 5,344,622 A | 9/1994 | Faddis et al. | |
| 5,540,898 A | 7/1996 | Davidson | |
| 5,897,831 A | 4/1999 | Jacob et al. | |
| 6,007,785 A | 12/1999 | Liou | |
| 6,110,431 A | 8/2000 | Dunder | |
| 6,270,733 B1 | 8/2001 | Rodden | |
| 6,331,279 B1 | 12/2001 | Martin | |
| 6,601,602 B2 | 8/2003 | Adler et al. | |
| 6,679,419 B1 | 1/2004 | Sarracino | |
| 6,866,142 B2 | 3/2005 | Lamborne et al. | |
| 7,104,289 B2 | 9/2006 | Daoud et al. | |
| 2003/0165411 A1 | 9/2003 | Engelhard | |
| 2004/0162527 A1* | 8/2004 | Moersdorf | A61M 5/178 604/199 |
| 2005/0074501 A1 | 4/2005 | Murphy et al. | |
| 2006/0073069 A1* | 4/2006 | Montgomery | A61M 1/0281 422/44 |
| 2006/0185668 A1* | 8/2006 | Jagger | A61M 16/101 128/201.21 |
| 2007/0025890 A1 | 2/2007 | Joshi et al. | |
| 2007/0154363 A1* | 7/2007 | Joshi | A61B 17/3478 422/186.04 |

FOREIGN PATENT DOCUMENTS

| | | |
|---|---|---|
| DE | 3119581 A1 | 12/1982 |
| GB | 261970 A | 12/1926 |
| WO | 99/37233 A1 | 7/1999 |
| WO | 01/41666 A1 | 6/2001 |
| WO | 2004103452 A1 | 12/2004 |

OTHER PUBLICATIONS

Chinese Office Action dated Dec. 4, 2012 issued in corresponding Chinese Patent Application No. 200880126715.4, with English translation to indicate the degree of relevance to the reference.
International Search Report dated Mar. 27, 2009 from corresponding International Appiication No. PCT/US2008/012027; 5 pgs.
Australian Patent Examination Report No. 2; Patent Application No. 2008336195 dated Oct. 8, 2013.

* cited by examiner

SYRINGE DEVICE, SYSTEM AND METHOD FOR DELIVERING OZONE GAS

RELATED APPLICATIONS

This application is a divisional of U.S. patent application Ser. No. 12/000,374 entitled SYRINGE DEVICE, SYSTEM AND METHOD FOR DELIVERING OZONE GAS, filed Dec. 12, 2007, the entire contents of which are hereby incorporated by reference.

BACKGROUND

Ozone is an unstable gas with a half-life of less than one hour at room temperature. Ozone is a powerful oxidizer. It is a known bactericide and viricide. Methods for converting oxygen to ozone involve high-voltage corona discharge or ultraviolet light. Ozone generators making use of such methods are available for industrial uses.

Ozone has a variety of industrial applications. Applications include deodorizing air, purifying water and sterilizing medical instruments, among others. Ozone and conventional medical ozone generators are being used therapeutically in many countries and have been so for several years. Such applications include, but are not limited to, autohemotherapy, rectal insufflations, intradiscal injection, injection into knee and shoulder joints, and full body exposure.

For example, ozone is used to treat diffuse bulging or contained herniation of the spinal disc. Spinal discs are composed of a fibrous outer ring made of Type I collagen and a softer more flexible nucleus made of Type II collagen, proteoglycans and water. Patients with disc bulging or herniation suffer from pain caused by disc compression of the neurological elements, including the spinal cord, cauda equina and nerve roots. Intradiscal ozone treatment involves direct injection of a gaseous mixture of oxygen and ozone into the nucleus of the disc. Ozone releases water from the proteoglycans, reducing disc size and relieving compression of neurological elements. Some investigators believe that ozone stimulates anti-inflammatory mediators and initiates a healing response.

The mechanism of action and reported success rates of ozone treatment for spinal disc herniation are comparable to that of the enzyme chymopapain. Chymopapain was first FDA-approved in 1983 and was widely used with a success rate of 65-85%. A small number of serious complications, including death and paralysis, caused the product to lose favor in the U.S. market.

Ozone and chymopapain are two means of performing a chemical discectomy through a needle puncture. This minimally invasive approach may be preferred to surgical discectomy, which requires general anesthesia and direct access to the spinal disc.

Therapeutic ozone must be delivered shortly after being produced from oxygen. Conventional medical ozone generators pass medical grade oxygen through an electric field or ultraviolet light. This process converts an amount of oxygen into ozone. Typically, a syringe is interfaced with the generator and ozone is withdrawn from a gas chamber of the generator into the syringe for subsequent injection therapy. Often, a spinal needle is already positioned within a patient and then the syringe is placed in fluid communication with the needle for injection.

The preferred concentration of ozone for intradiscal injection is approximately 6%. The concentration of ozone is important for medical uses. If the concentration is too low, the treatment will not be effective. If the concentration of ozone is too high, detrimental effects may follow.

As such, medical ozone generators include a means for measuring the concentration of ozone. Conventional ozone generators also have means for controlling the concentration and delivery of ozone gas. For example, some generators include components that neutralize excess ozone. Other generators continuously vent ozone.

Conventional ozone generators typically include permanent and reusable electrodes. The gas chambers of conventional generators are often permanent and reusable as well. Reusable electrodes tend to degrade over time. Sterility is an issue for present ozone generators that pass oxygen through permanent and reusable gas chambers. The bioburden of these machines is unknown. Thus, the ability of ozone to sterilize these components cannot be validated. To address such, medical professionals have been known to inject the gas through a bacterial filter but compliance with this practice is sporadic as filters may not be available or the clinician may be trying to minimize equipment cost.

SUMMARY

According to at least one exemplary embodiment, a syringe device for producing an amount of ozone from oxygen can include a syringe having a plunger slidably engaged with a barrel. The barrel and the plunger can cooperate to define a gas chamber. A case for providing substantial sterility can be configured to enclose the syringe. The syringe device can be configured to interface with an ozone generator.

In another exemplary embodiment, a method of producing an amount of ozone from oxygen for administering to a person can include providing a valvably-controlled fluid channel extending from a syringe through a sterility case enclosing the syringe. A gas chamber of the syringe can be filled with substantially pure oxygen gas via the valvably-controlled fluid channel. An electric current can be provided to one or more conductive elements on the sterility case. The one or more conductive elements can be connected to one or more electrodes. The one or more electrodes can be attached to the syringe. A corona discharge can be effectuated from at least one electrode. An amount of ozone gas can be produced from the oxygen gas.

In yet another exemplary embodiment, an ozone generation system can include a syringe device having a syringe enclosed by a sterility case. One or more electrodes can be attached to the syringe. One or more conducting elements can be on the sterility case. The one or more conducting elements can be directly or indirectly connected to the one or more electrodes. An ozone generator with a high voltage supply can be configured to provide current to the one or more conducting elements.

BRIEF DESCRIPTION OF THE FIGURES

Advantages of embodiments of the present invention will be apparent from the following detailed description of the exemplary embodiments thereof, which description should be considered in conjunction with the accompanying drawings in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the terms "embodiments of the invention", "embodiment" or "invention" do not require that all embodiments of the invention include the discussed feature, advantage or mode of operation.

Figure 1:
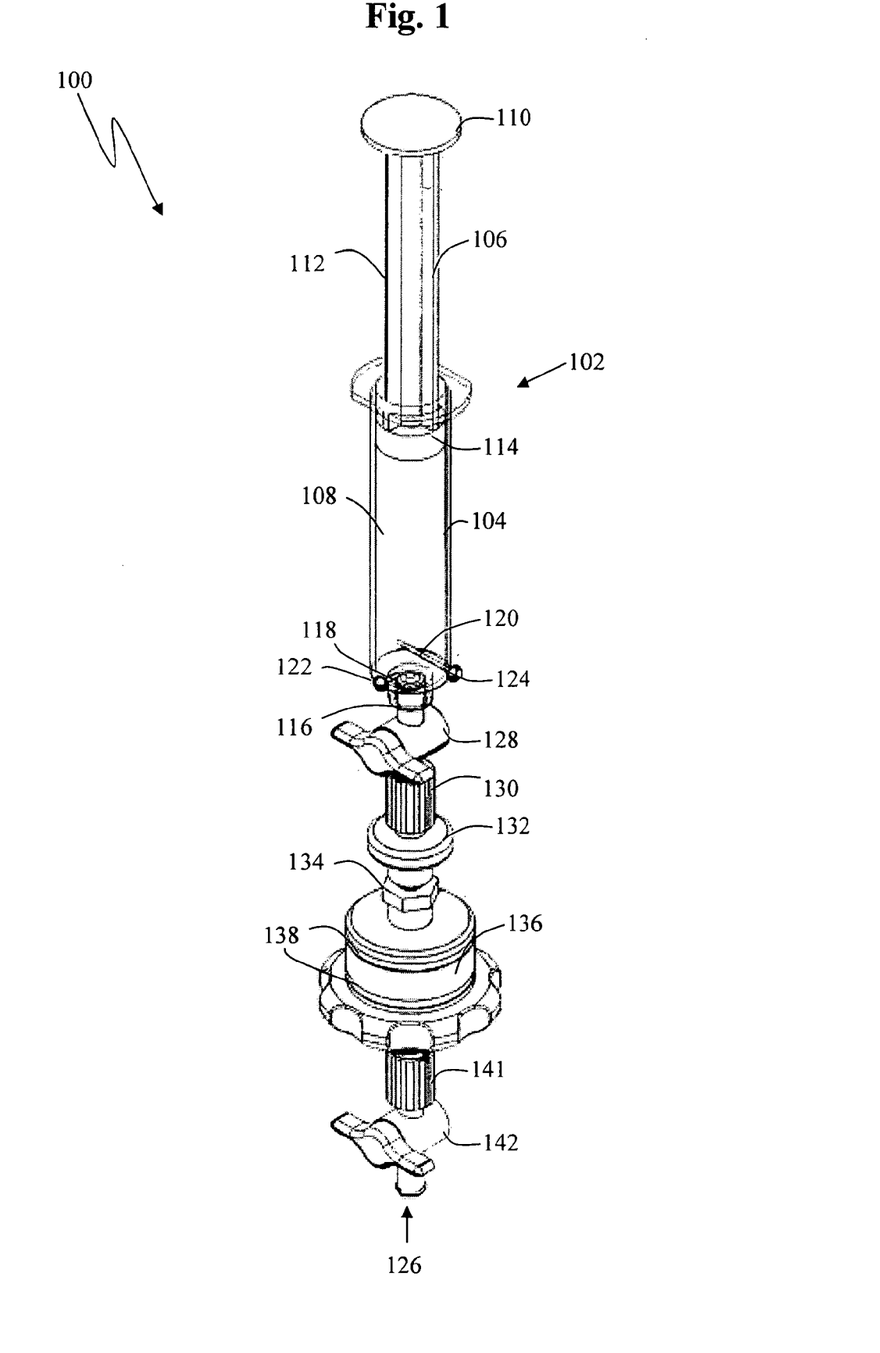
FIG. 1 is a perspective view of an exemplary syringe device.
Figure 2A:
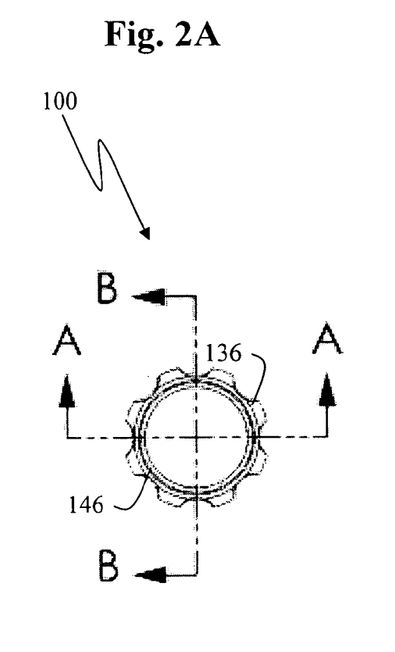
FIG. 2A is a top view of the exemplary syringe device of FIG. 1 that further includes an exemplary sterility case.
Figure 2B:
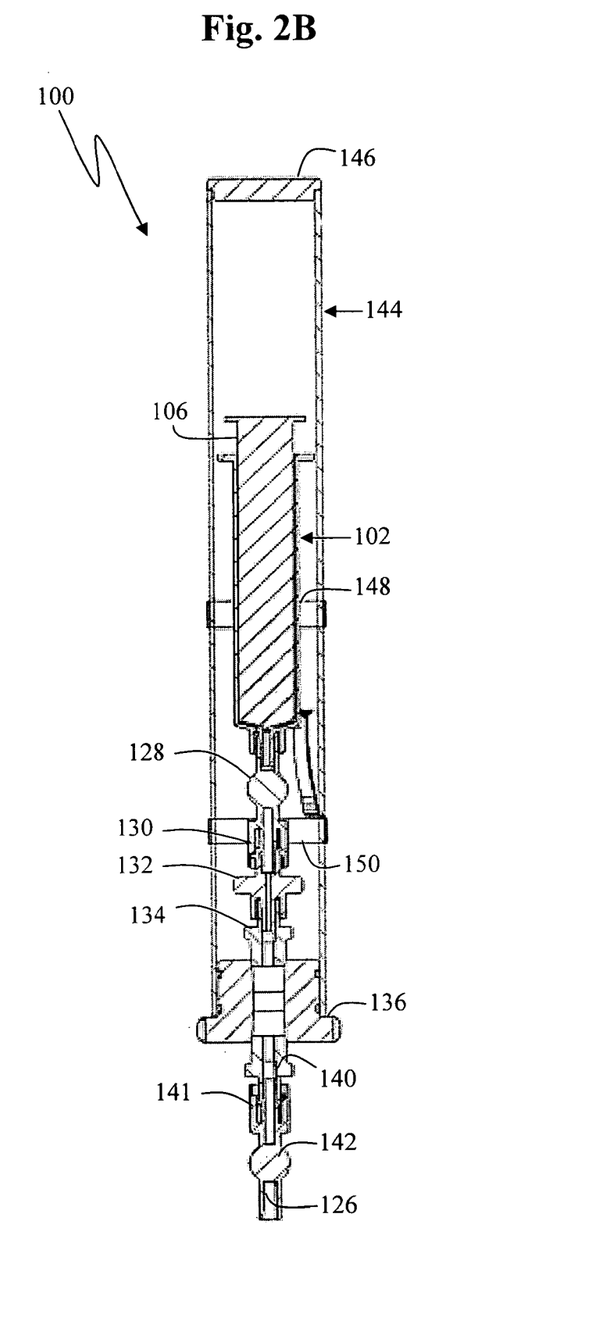
FIG. 2B is a cross-sectional view along line A of FIG. 2A.
Figure 2C:
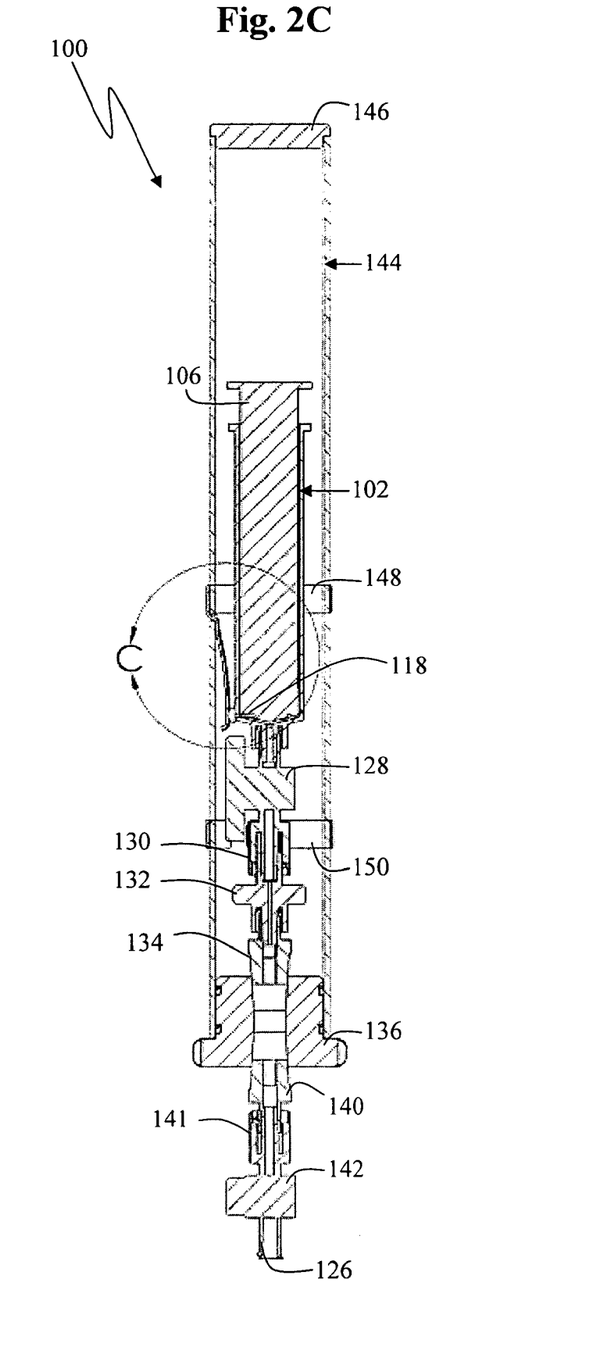
FIG. 2C is a cross-sectional view along line B of FIG. 2A.
Figure 2D:
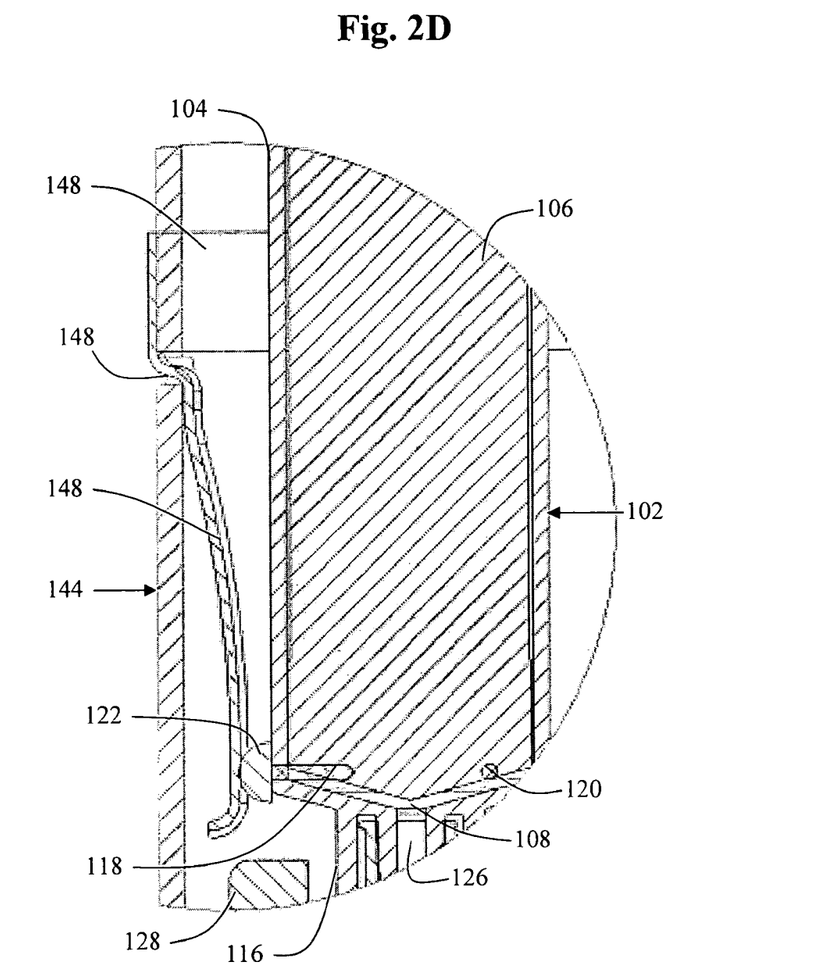
FIG. 2D is an enlarged view of the portion circumscribed by line C of FIG. 2C.

Referring to FIG. 1, a syringe device (without a sterility case portion) in accordance with at least one exemplary embodiment is shown. Syringe device 100 (or any portion thereof) can be single-use and may be reprocessable. Alternatively, syringe device 100 (or any portion thereof) may be multi-use with sterilization, although such embodiments would stray from current trends in healthcare. Syringe device 100 can be fabricated, in whole or in part, by any conventional molding processes known to one having ordinary skill in the art. Syringe device 100 can serve as a cell for producing an amount of ozone from oxygen when used with a suitable ozone conversion unit, as further described below. Optionally, syringe device 100 can be filled with substantially pure (e.g., medical grade) oxygen using a zeolite-based oxygen concentrator, as further described below. An ozone conversion unit and zeolite-based oxygen concentrator can be provided for in one unit that can operatively engaged syringe device 100. Syringe device 100, particularly, syringe portion 102 fitted (directly or indirectly) with a hypodermic needle can be used to administer a therapeutic amount of ozone to a human or an animal, as will be readily recognized by one having ordinary skill in the art.

Syringe portion 102 of syringe device 100 can include barrel 104, plunger 106 and gas chamber 108. Gas chamber 108 can be defined and bounded through the cooperation of barrel 104 and plunger 106. In at least one exemplary embodiment, syringe portion 102 can be sized to hold between 10 ml and 30 ml of fluid in gas chamber 108, including between 10 ml and 30 ml of medical grade oxygen.

Barrel 104 can be made of any suitable material that allows for at least some UV transmission. This can allow for the passage of a UV beam through barrel 104 and a gas within gas chamber 108 for measuring the concentration of ozone gas. Furthermore, barrel 104 can be constructed of any material that sufficiently balances the needs for ozone resistance and UV resistance while still allowing for suitable UV transmission for measuring the concentration of ozone. Flexibility in construction can be increased because syringe device 100 may only be exposed to ozone and UV light for a shortened/decreased period of time.

For example, barrel 104 (in which, syringe portion 102, as a whole, can be constructed largely or wholly of the same) can be constructed of polyethylene, polytetraflouroethylene ("PTFE", TEFLON®), polyacrylate (acrylic polymers), polycarbonate, polystyrene, styrene copolymers, polypropylene and the like known to one having ordinary skill in the art. Barrel 104 can also be made of glass, as one more non-limiting example. In at least one exemplary embodiment, barrel 104 can be made of polyethylene even though polyethylene may only allow about 10% UV transmission. A UV transmission of about 10% can be enough to measure ozone concentration within gas chamber 108 with suitable accuracy.

Plunger 106 can be slidably engaged with a first open end (i.e. top end) of barrel 104. The engagement of plunger 106 with barrel 104 can define the bounds of gas chamber 108 within syringe portion 102. Through sliding movements of plunger 106 within barrel 104, a fluid, including a gaseous fluid (e.g., oxygen gas), can be drawn into and expelled from gas chamber 108. Plunger 106 can include a plunger head 110 on one end of plunger shaft 112. On the other end of plunger shaft 112 can be plunger piston 114. Plunger piston 114 can form a gas-tight seal with barrel 104. Plunger piston 114 may be made from or covered with rubber and the like known to one having ordinary skill in the art. Tip portion 116 of syringe portion 102 can extend in fluid communication from a second end of barrel 104.

Wire electrodes 118, 120 can extend inwardly within barrel 104. Wire electrodes 118, 120 may be made to extend inwardly by providing wire electrodes 118, 120 through barrel 104. Wire electrodes 118, 120 can be provided through barrel 104 in a gas-tight manner. Wire electrodes 118, 120 can be situated proximate the end of barrel 104 from which tip portion 116 can extend from. Placing wire electrodes 118, 120 towards the tip end (i.e. bottom end) of barrel 104 can assist or prevent plunger 106 and wire electrodes 118, 120 from interacting in a non-beneficial manner, such as causing damage to or misplacement of either, or compromising the gas-tight sealing functionality of plunger piston 114, leading to leakage.

Wire electrodes 118, 120 can be made of any suitable conductive material known to one having ordinary skill in the art. Wire electrodes 118, 120 may be solid metal rods of a relatively simple construction, which may be cost-effective. In addition, a dielectric material may cover a portion(s) of wire electrode 118 and/or 120 in at least one exemplary embodiment.

Wire electrode 118 can extend inwardly towards the center of hollow barrel 104 (i.e. the center of gas chamber 108). Wire electrode 118 may breach barrel 104 once and may retain a gas-tight seal proximate the breach. Wire electrode 118 can approach the center of gas chamber 108 in cross-section. Wire electrode 118 can be the discharge electrode. The end of wire electrode 118 situated within gas chamber 108 can form a sharp point. Alternatively, the end of wire electrode 118 can be blunt.

Wire electrode 120 can extend inwardly and can transverse a cross section of gas chamber 108. Wire electrode 120 can be straight (as shown) or can be curved. Wire electrode 120 may breach barrel 104 twice and may retain gas-tight seals proximate the breaches. Wire electrode 120 may transverse a cross section of gas chamber 108 off-center. Wire electrode 118 and wire electrode 120 can exist in a substantially perpendicular relationship without contacting one another. In other words, wire electrode 118 and wire electrode 120 can extend from and/or enter barrel 104 at approximately a right angle. Wire electrodes 118, 120 can also be disposed at substantially the same planar orientation in cross-section. Wire electrode 120 can be the ground electrode for completing a circuit and may be used to sustain the current flow.

Electrical contact points 122, 124 can be disposed on the outside of barrel 104, as well as various other positions, as will be readily recognized to one having ordinary skill in the art. Electrical contact point 122 can be connected with wire electrode 118. Electrical contact point 122 may be an integral portion of wire electrode 118. Electrical contact point 124 can be disposed on an end of wire electrode 120 outside of syringe portion 102. Electrical contact point 124 can be connected to wire electrode 120 and may be an integral portion thereof.

Electrical contact points 122, 124 can be indirectly connected (described below) to an ozone generation unit for effectuating a corona discharge via wire electrodes 118, 120. Wire electrode 118 can be the discharge electrode and wire electrode 120 can be the ground electrode. The corona discharge can be used to produce an amount of ozone gas from oxygen gas within gas chamber 108. A user can predetermine the amount (e.g., concentration) of ozone desired through operation of a suitable ozone conversion unit. For example, therapeutic levels for intradiscal injection may be up to 6% ozone gas by volume and such concentrations may be selected by a user of a suitable ozone conversion unit.

In other embodiments, a pair of electrodes (and portions forming electrical contact points) can be provided in a variety of configurations. Moreover, either one or both of the pair of electrodes can be foil electrodes. Further, either one or both of the pair of the electrodes can be positioned wholly outside of syringe portion 102. Pending U.S. patent application Ser. No. 11/976,362 (incorporated by reference below) discloses exemplary configurations for a pair of electrodes attached to syringe portion 102 and may be referred to for guidance.

In at least one exemplary embodiment, wire electrode 118 can be paired with a foil electrode. The foil electrode can be disposed on a portion of the inner wall of barrel 104. The foil electrode can be curved, for example, consistent with the curvature of the inner wall of barrel 104. Alternatively, the foil electrode can be linear. The foil electrode can be relatively thin as is a known characteristic of foil electrodes in general. The foil electrode can be situated towards the tip end (bottom end) of barrel 104. Foil electrode 222 can be the ground electrode.

An electrical contact point for the foil electrode can be disposed on the outside of barrel 104, as well as various other positions, as will be readily recognized by one having ordinary skill in the art. The electrical contact point can be situated on a bottom portion of barrel 104. The electrical contact point can be connected to the foil electrode and may be an integral portion of foil electrode. The foil electrode can be a one-piece insert having the electrical contact point. The foil electrode can breach barrel 104 so as to have a face on a portion of the wall of barrel 104 and the electrical contact point on the outside of barrel 104. The foil electrode can breach barrel 104 in a gas-tight manner.

In another exemplary embodiment, wire electrode 118 can be paired with a foil electrode attached on the outer wall of barrel 104 by any means known to one having ordinary skill in the art. The foil electrode can be situated proximate the bottom end (tip end) of barrel 104. Wire electrode 118 can extend towards and approach a face of the foil electrode with a portion of barrel 104 interposed there between. The foil electrode can be the ground electrode.

In yet another exemplary embodiment, a pair of wire electrodes can be configured in a substantially opposing relationship with one another. The wire electrodes can extend inwardly within barrel. The wire electrodes may be made to extend inwardly by providing wire electrodes through barrel 104. The wire electrodes can be provided through barrel 104 in a gas-tight manner.

The wire electrodes can extend inwardly towards the center of barrel 104. The wire electrodes can approach the center of gas chamber in cross-section. The wire electrodes can exist in a substantially opposing relationship without contacting one another. The wire electrodes may also be disposed at substantially the same planar orientation in cross-section. Each of the wire electrodes may breach barrel 104 once and may retain a gas-tight seal proximate the breach.

Either of the wire electrodes can be the discharge electrode depending on the connection to an ozone conversion unit. The other electrode can then function as the ground electrode. The ends of wire electrodes situated within gas chamber 108 can form a sharp point. Alternatively, the ends of the wire electrodes can be blunt or a combination of one sharp end and one blunt end, respectively.

Each electrical contact point of each electrode can be disposed on the outside of barrel 104, as well as various other positions, as will be readily recognized to one having ordinary skill in the art. The electrical contact points can be respectively connected with the wire electrodes and may be integral portions thereof.

In yet another exemplary embodiment, a pair of substantially opposing wire electrodes can be angled. The electrodes can be angled downwards proximate the inner bottom portion of barrel 104, thus, not strictly occupying substantially the same planar orientation in cross-section. As a result, the bottom portion of a barrel 104 can be shaped so as to accommodate angled electrodes. For example, barrel 104 can be shaped to have a conical bottom portion.

In a further exemplary embodiment, syringe portion 102 can include a pair of foil electrodes. The foil electrodes can be elongated and generally resembling strips in configuration. The foil electrodes can be disposed on the inner wall of barrel 104. Alternatively, in at least one other exemplary embodiment, the foil electrodes can be disposed on portions of the outer wall of barrel 104.

The foil electrodes can be disposed on opposing portions of the inner wall of barrel 104. A face of each of the foil electrodes can be in an opposing relationship. Also, the foil electrodes may vertically transverse a midportion of barrel 104.

The electrical contact surfaces/points can be disposed on the outside of barrel 104, as well as various other positions, as will be readily recognized by one having ordinary skill in the art. The electrical contact surfaces can be situated on opposite side portions of barrel 104. The electrical contact surfaces can be respectively connected to the foil electrodes and may be integral portions thereof.

The foil electrodes can be one-piece inserts (e.g., molded inserts) having the electrical contact surfaces. The foil electrodes can breach barrel 104 so as to have a face on a portion of the inner wall of barrel 104 and the electrical contact surfaces on the outside of barrel 104. The foil electrodes can breach barrel 104 in a gas-tight manner. Either of the foil electrodes can be the discharge electrode depending on the connection to an ozone conversion unit. The other electrode can then function as the ground electrode.

Referring to FIG. 1 and FIGS. 2A-2D, valvably-controlled fluid channel 126 can extend in fluid communication from tip portion 116 of syringe portion 102. Valvably-controlled fluid channel 126 can be provided through the cooperation of multiple valves and other fittings known to one having ordinary skill in the art. Alternatively, valvably-controlled fluid channel 126 can be provided by an integral structure (not shown). Valvably-controlled fluid channel 126 can be connected to syringe portion 102 in a variety of manners for providing valvably-controlled fluid communication with gas chamber 108, as will be readily recognized by one having ordinary skill in the art.

As shown, valvably-controlled fluid channel 126 can be provided through the cooperation of first stopcock valve 128, first luer fitting 130, filter 132, second luer fitting/adaptor 134, sterility cap 136 with O-rings 138, third luer fitting/adaptor 140, fourth luer fitting 141 and second stopcock valve 142. All or less than all of the valves and other fittings can be coupled in a removable manner. First stopcock valve 128 can be fitted onto tip portion 116. First luer fitting 130 can couple first stopcock valve 128 to filter 132. Second luer fitting/adapter 134 can couple sterility cap 136 to filter 132. Luer fittings 140, 141 can be used to couple second stopcock valve 142. Alternatively, fourth luer fitting 141 or any other suitable fitting known to one having ordinary skill in the art can be connected to an oxygen supply source for filling, such as an oxygen tank or hospital supply line, as a couple non-limiting examples. Luer fittings 130, 134, 140, 141 can be press-on, twist-on and the like. In further embodiments, other fittings and valves known to one of ordinary skill in the art can be used to provide valvably-controlled fluid channel 126.

Filter 132 can be any suitable filter for protecting gas chamber 108 from contamination known to one having ordinary skill in the art. For example, suitable filters can include the QOSINA hydrophobic filter with a pore size of 5 μm and the MILLIPORE® Aervent-50 hydrophobic filter with a pore size of 0.2 μm. Smaller pore size provides greater filtration but requires greater pressure to push gas into gas chamber 108 of syringe portion 102. Both filters contain a PTFE membrane in a polypropylene casing. After ozone generation and prior to injection, sterility case 144 and filter 132 can be removed. By disengaging filter 132, removed contaminants trapped by filter 132 are not forced back by reverse flow into the patient during injection.

By providing filter 132 within sterility case 144, a clinician does not have the option of removing filter 132 without removing sterility case 144, thus destroying the integrity of syringe device 102, if sterility case 144 is removed prior to ozone conversion. Thus, filter 132 can be used as an integrated part of syringe device 102 until sterility case 144 is removed after ozone generation and prior to injection. This may be beneficial because clinician will use filter 132, which is believed to be best practice. It may be convenient as filter 132 can already be provided as an integrated part of syringe device 102. It may also urge the industry to adopt filtration as a standard industry-wide practice, which may benefit the industry as a whole.

Sterility cap 136 can have a male portion and a grip portion. The male portion can be designed to be inserted into an open end of sterility case 144 in snug engagement. The male portion may be cylindrical if sterility case 144 is tubular, as one non-limiting example. Snug engagement of sterility cap 136 and sterility case 144 can form a seal, which may or may not be gas-tight. One or more O-rings 138 can be disposed around the male portion of sterility cap 136 for facilitating snug engagement and can promote the formation of a seal between sterility cap 138 and sterility case 144.

During snug engagement, the grip portion of sterility cap 136 can border sterility case 144 and may project laterally in all directions. The grip portion of sterility cap 136 can be circular. The grip portion of sterility cap 136 can provide a useful area for a user to manipulate sterility cap 136 to engage or disengage with sterility case 144. The grip portion may be contoured or textured for increased ease in manipulation by a user's hands and fingers.

Sterility cap 136, as a whole, can have a channel defined through it, which can form a portion of valvably-controlled fluid channel 126. When sterility cap 136 is engaged with sterility case 144, valvably-controlled fluid channel 126 can extend from tip portion 116 through sterility cap 136 and, hence, through sterility case 144 because sterility cap 136 can be viewed as a component thereof during engagement.

Referring particularly to FIGS. 2A-2D, the syringe device of FIG. 1 is shown with a sterility case portion in accordance with at least one exemplary embodiment. Syringe device 100 can include sterility case 144. Sterility case 144 can be rigid, flexible or any combination thereof. In at least one exemplary embodiment, sterility case 144 can be made of a rigid plastic material. Sterility case 144 can be tubular in shape, as one non-limiting example.

Sterility case 144 can prevent direct handling and other types of physical contact with syringe portion 102. By preventing direct handling and other types of physical contact, sterility case 144 can decrease the likelihood of contamination. Particularly, incidences of contamination of gas chamber 108 can be reduced. Thus, the mere existence of sterility case 144 as a physical barrier may provide substantial sterility to syringe portion 102. Sterility case 144 may or may not be gas-tight. A gas-tight seal may provide additional safeguards against contamination of gas chamber 108. Overall, sterility case 144 can increase the likelihood of a sterile dose of ozone being delivered to a patient.

As shown, sterility case 144 can be engaged with sterility cap 136 so as to house syringe portion 102, a portion of valvably-controlled fluid channel 126, first stopcock valve 128, first luer fitting 130, filter 132 and second luer fitting/adaptor 134 in a ship-in-a-bottle configuration. Sterility case 144 may or may not be sealed in a gas-tight manner at its top end. For example, sterility case 144 can be sealed by sterility end cap 146, which can be considered a component of sterility case 144. Alternatively, sterility case 144 can have an integral top portion. The components and portions housed within sterility case 144 can remain substantially sterile after sterilization of syringe device 100 because of the physical barrier provided by sterility case 144. Sterilization can be performed by gamma irradiation or any other method known to one having ordinary skill in the art. After sterilization, syringe device 100 can be packaged in Tyvek pouch, as one non-limiting example. Gas chamber 108 can remain substantial sterile when fluid communication is obstructed through the operation of one or more valves of valvably-controlled fluid channel 126 and/or by retaining plunger 106 in a depressed state. Filter 132 can also prevent contamination when fluid communication is or is not obstructed.

Sterility case 144 (or portions thereof) can be made of any suitable material and may allow for at least some UV transmission. UV transmissibility can allow for the passage of a UV beam through sterility case 144, barrel 104 (also having some UV transmissibility) and a gas within gas chamber 108 for measuring the concentration of ozone gas.

For example, sterility case 144 can be constructed of polyacrylate because of its UV transmission properties. In other embodiments, sterility case 144 can be constructed of polyethylene, polytetraflouroethylene ("PTFE", TEFLON®), polycarbonate, polystyrene, styrene copolymers, polypropylene and the like known to one having ordinary skill in the art. Sterility case 144 can also be made of glass, as one more non-limiting example.

First conducting element 148 and second conducting element 150 can be attached to or otherwise disposed on sterility case 144. Conducting elements 148, 150 can be of any conductive material, including various metals, known to one having ordinary skill in the art. As one non-limiting example, conducting elements 148, 150 can be made of beryllium copper alloy ("Be—Cu"). Conducting elements 148, 150 can each be a one-piece construction. Alternatively, conducting elements 148, 150 can have more than one piece, as will be readily recognized by one having ordinary skill in the art. Conducting elements 148, 150, whether one-piece or not, can have portions outside of and inside of, as well as a portion(s) in a breaching relationship with sterility case 144. Conducting elements 148, 150 may or may not breach sterility case 144 in a gas-tight manner. In exemplary embodiments, the holes required to pass conducting elements 148, 150 can be covered with tape or sealed with epoxy, as couple non-limiting examples, if conducting elements 148, 150 are not already passed in a gas-tight manner.

In single-use embodiments, a fuse (not shown) or interfering electrical contacts can be coupled to one or more of conducting elements 148, 150. The fuse can be used as one means for identifying that syringe device 100 has been previously used. Alternatively, singularly or in conjunction, one or both of conducting elements 148, 150 can "spring" out when the syringe device 100 is removed from a suitable ozone conversion unit.

Conducting elements 148, 150 can be fashioned in a variety of shapes and dimensions. As shown, conducting elements 148, 150 can each have a ring-shaped outer portion and a projecting portion for breaching sterility case 144. The projecting portion can be shaped (e.g., curved and/or bent) so as to respectively reach and contact one of electrical contact points 122, 124 when sterility case 144 is engaged with sterility cap 136.

When sterility case 144 is engaged with sterility cap 136, conducting element 148 can contact electrical contact point 122 and conducting element 150 can contact electrical contact point 124 for providing current. Conducting elements 148, 150 can be electrical contact points in their own right for interfacing with electrical contact points of a medical ozone generator. A medical ozone generator can supply electrical current through conducting elements 148, 150 and, in turn, through electrodes 118, 120 in order to effectuate corona discharge. The corona discharge can be used to produce an amount of ozone gas from oxygen gas within gas chamber 108. A user can predetermine the amount (e.g., concentration) of ozone desired through operation of a suitable ozone conversion unit. For example, therapeutic levels for intradiscal injection may be up to 6% and such concentrations may be selected by a user of a suitable ozone conversion unit.

Figure 3A:
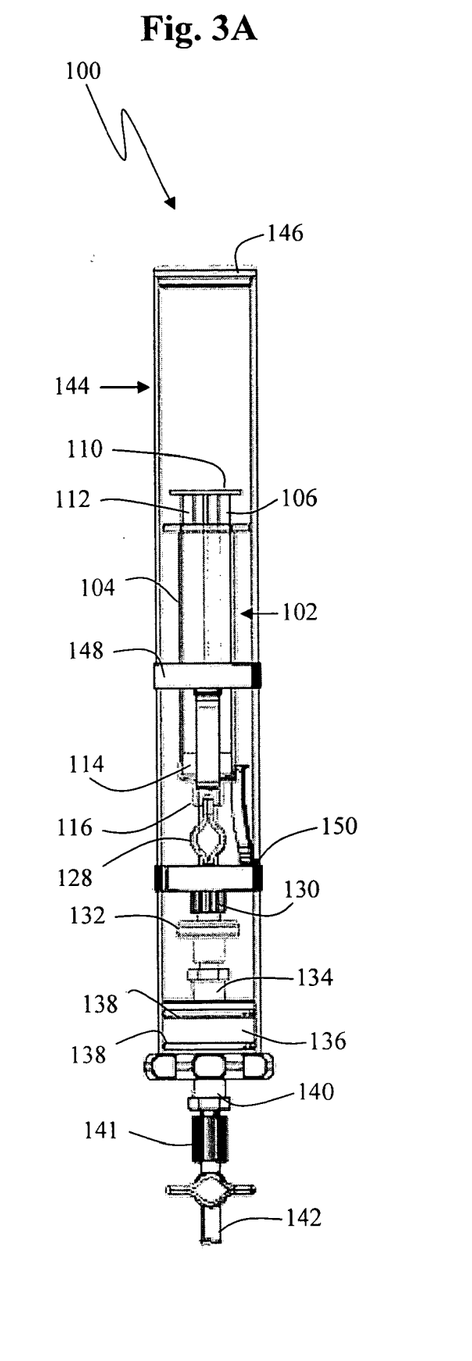
FIG. 3A is a side view of the exemplary syringe device of FIGS. 2A-2D in an initial state.

Referring to FIGS. 3A-3E, syringe device 100 is shown in various configurations for different states of use. Referring particularly to FIG. 3A, syringe device 100 is shown in a pre-use or initial state. Syringe device 100 can be provided as such, for example, from a manufacturer or vendor to a user. A user can be a clinician, such as a doctor or other medical personnel. Syringe device 100 can be provided from a manufacturer or vendor in a substantially sterile state. For example, syringe device 100 can be provided in sterile packaging, such as a sterile pouch. Sterilization can be performed by any method known to one having ordinary skill in the art, including gamma irradiation. Notably, plunger 106 can be provided in a depressed state. Second stopcock valve 142 can be in a closed state to prevent contaminating valvably-controlled fluid channel 126.

Figure 3B:
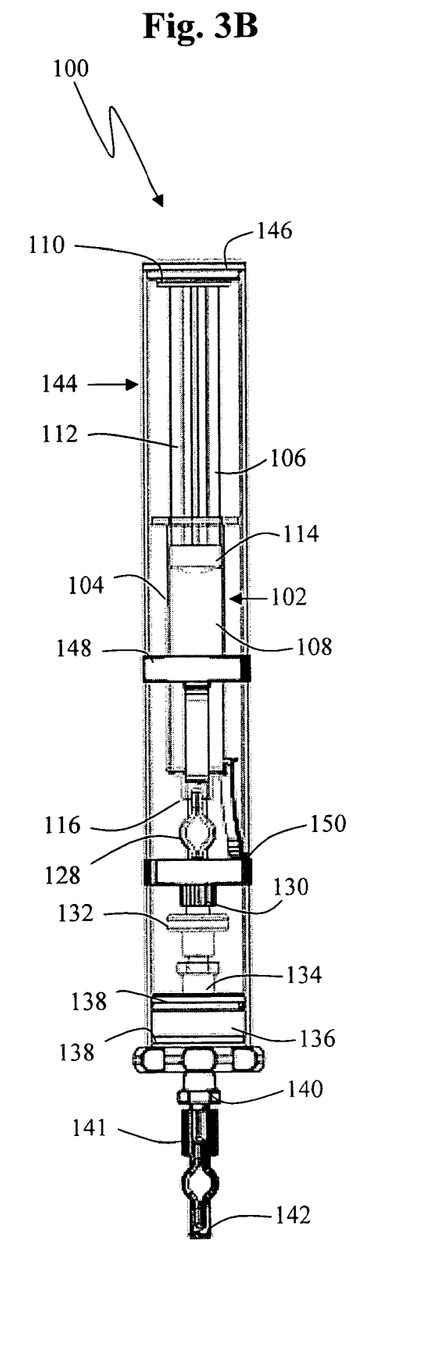
FIG. 3B is a side view of the exemplary syringe device of FIGS. 2A-2D in a filled state.

Referring particularly to FIG. 3B, syringe portion 102 of syringe device 100 can be filled with substantially pure oxygen gas (e.g., medical grade oxygen) via valvably-controlled fluid channel 126 and, thereafter, an amount of ozone gas can be produced from the oxygen gas in gas chamber 108. In at least one exemplary embodiment, syringe device 100 can be connected to an oxygen concentrator for filling gas chamber 108 with substantially pure oxygen gas. The oxygen concentrator can be part of the same unit as an ozone conversion unit. In another embodiment, syringe device 100 may be pre-filled with oxygen, sealed in a sterility case and then sterilized and packaged, in which case the sterility cap would not require a gas passage.

The oxygen concentrator can be consistent with any embodiment disclosed by U.S. patent application Ser. No. 11/976,362 (incorporated by reference below). Second stopcock valve 142 can be manipulated to provision concentrated and substantially pure oxygen gas via valvably-controlled fluid channel 126 to gas chamber 108 when syringe device 100 is connected to such a filling apparatus. Filling can occur by pressurizing at least one zeolite chamber with ambient air. The zeolite chamber can have at least one zeolite material that selectively sorts nitrogen from oxygen. Stopcock valve 142 can be set to the open position and syringe portion 102 (oxygen-ozone cell) can be filled with concentrated oxygen gas from the at least one zeolite chamber via valvably-controlled fluid channel 126. Filter 132 can decrease exposure of gas chamber 108 to contaminating agents.

Plunger 106 can be elevated during the filling process, whether being filled by an oxygen concentrator or other oxygen supply, due to pressure from the oxygen gas entering gas chamber 108. Gas chamber 108 can, thus, expand upon ingress of oxygen gas. Sterility end cap 146 (i.e. top end of sterility case 144) can act as a stopper for abutting plunger head 110 to ensure that plunger piston 114 of plunger 106 is retained within barrel 104.

Once filled by an oxygen concentrator or other oxygen supply, syringe device 100 can be operatively connected to an ozone generator, such as an exemplary ozone conversion unit disclosed in U.S. patent application Ser. No. 11/527,414 (incorporated by reference below). If the oxygen concentrator and ozone conversion unit are conjunctively housed, then there may be no need to disengaged syringe device 100. Alternatively, if the oxygen concentrator is a separate unit from the ozone conversion unit, then syringe device 100 can be disengaged from the oxygen concentrator and operatively coupled to an ozone conversion unit.

Conducting elements 148, 150 can be interfaced with electrical contact points of an ozone generator. A medical ozone generator can supply electrical current through conducting elements 148, 150 and, in turn, through electrodes 118, 120 in order to effectuate corona discharge. The corona discharge can be used to produce an amount of ozone gas from oxygen gas within gas chamber 108. A user can predetermine the amount (e.g., concentration) of ozone desired through operation of a suitable ozone conversion unit. Alternatively, an ozone generator relying on UV light for conversion can be used and conducting elements 148, 150, as well as wire electrodes 118, 120 may not be needed in such embodiments. Therapeutic levels for intradiscal injection may be up to 6% and such concentrations may be selected by a user of a suitable ozone conversion unit.

Figure 3C:
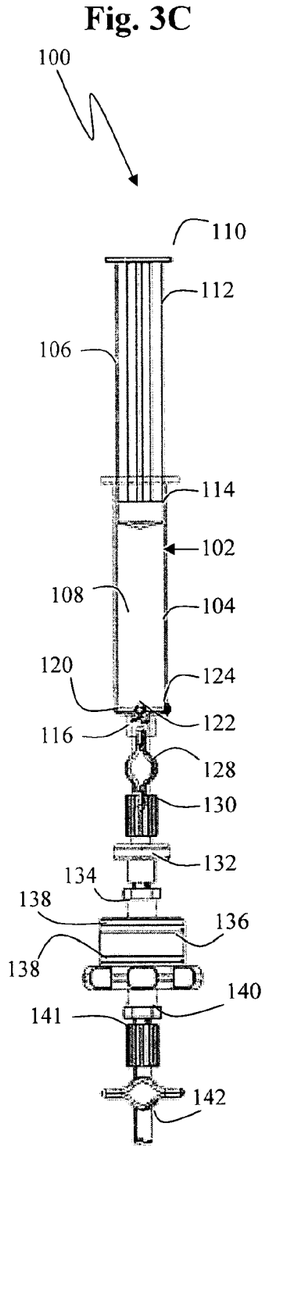
FIG. 3C is a side view of the exemplary syringe device of FIGS. 2A-2D with the exemplary sterility case detached.

Syringe device 100 can be disconnected from the ozone generator, which may be done shortly after ozone gas is produced. For example, the ozone-oxygen gaseous mixture for intradiscal injection should be delivered shortly after ozone gas is produced so that a significant amount of the ozone gas does not break down due to its short half-life. The ozone conversion unit can have the ability to hold the concentration of ozone at a specific level by delivering voltage if the concentration falls. Once the syringe device 100 is disconnected from the machine, a stopwatch function can be activated to encourage the clinician to complete the injection within a set time (e.g. three minutes). Second stopcock valve 142 can be closed to decrease exposure to contaminating agents as shown in FIG. 3C. Filter 132 can also function to decrease exposure to contaminating agents whether or not stopcock valve 142 is placed in a closed configuration.

Figure 3D:
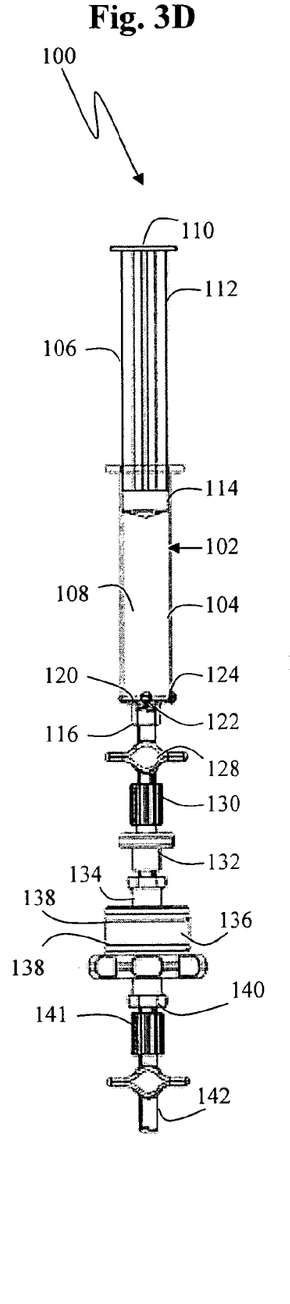
FIG. 3D is a side view of the exemplary syringe device of FIGS. 2A-2D with the exemplary sterility case detached and the exemplary stopcock valve in a closed state.
Figure 3E:
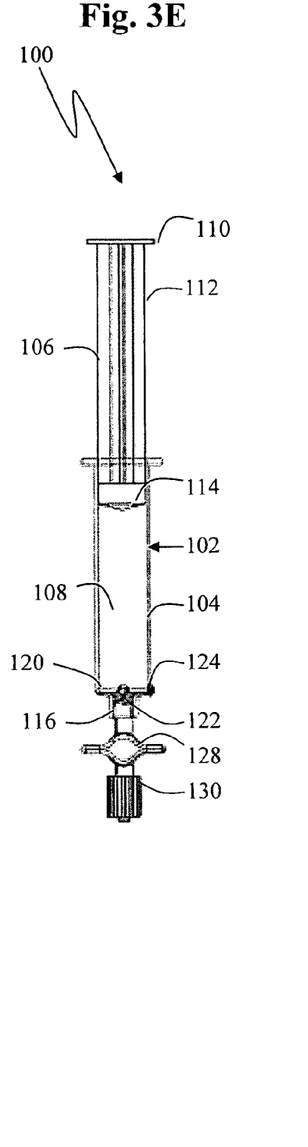
FIG. 3E is a side view of the exemplary syringe device of FIGS. 2A-2D with the exemplary sterility case detached and a portion starting at the exemplary filter detached.
Figure 4A:
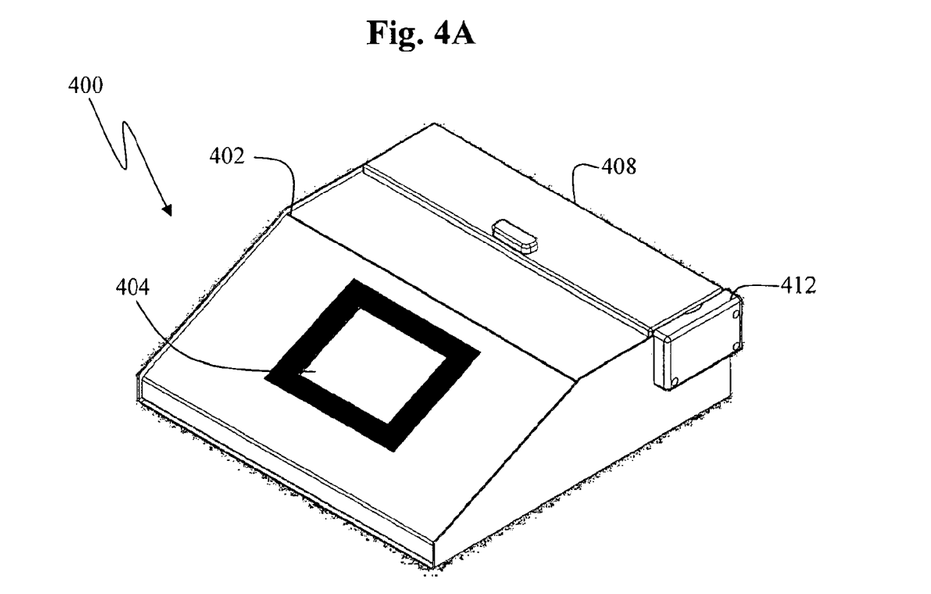
FIG. 4A is a perspective view of an exemplary ozone conversion unit.
Figure 4B:
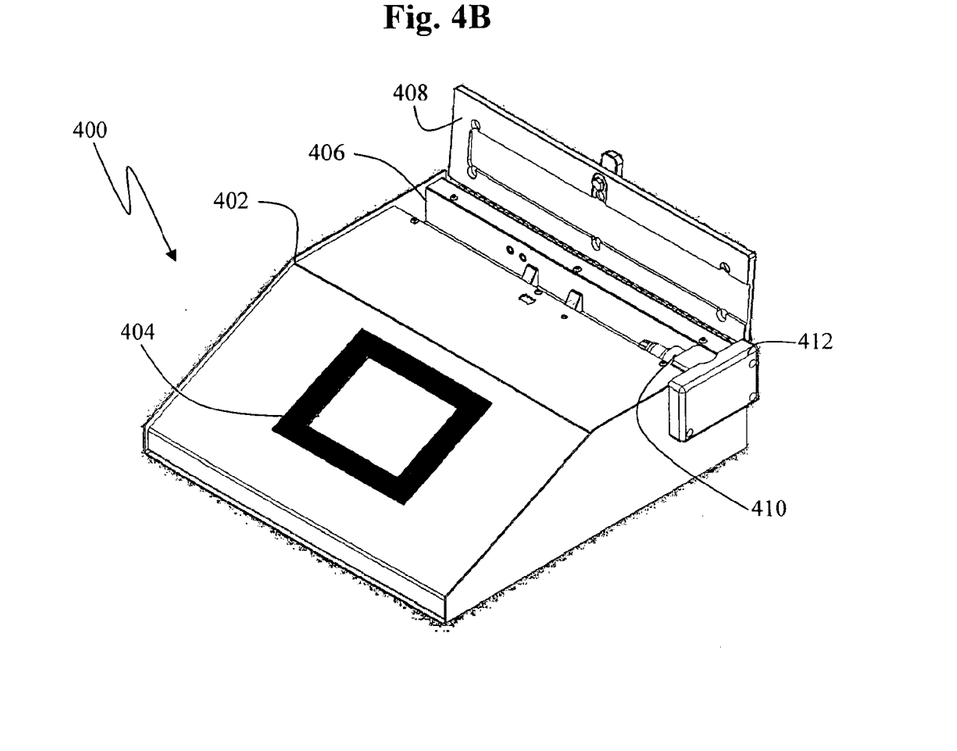
FIG. 4B is a perspective view of the exemplary ozone conversion unit with the lid in an open position.
Figure 4C:
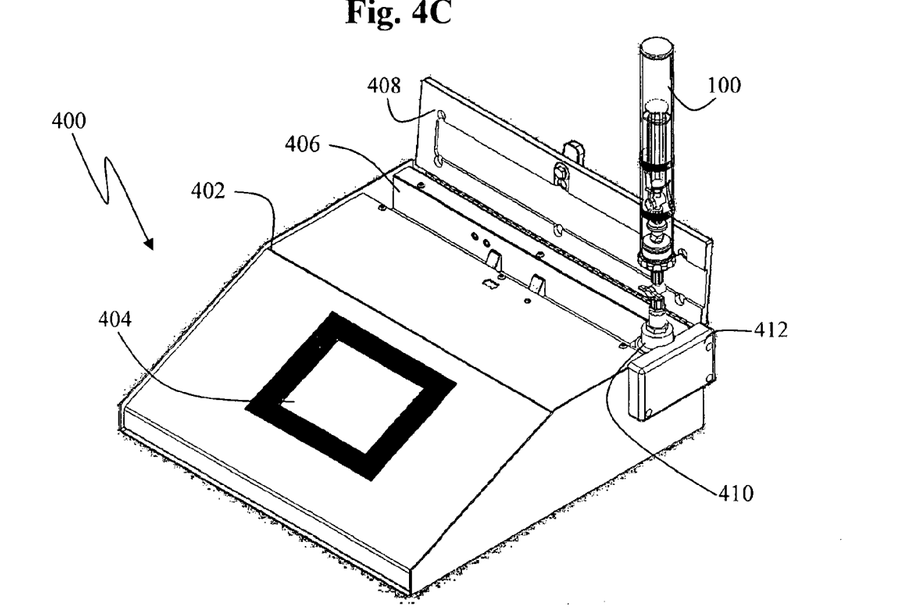
FIG. 4C is a perspective view of the exemplary ozone conversion unit cooperating with an exemplary syringe device.
Figure 4D:
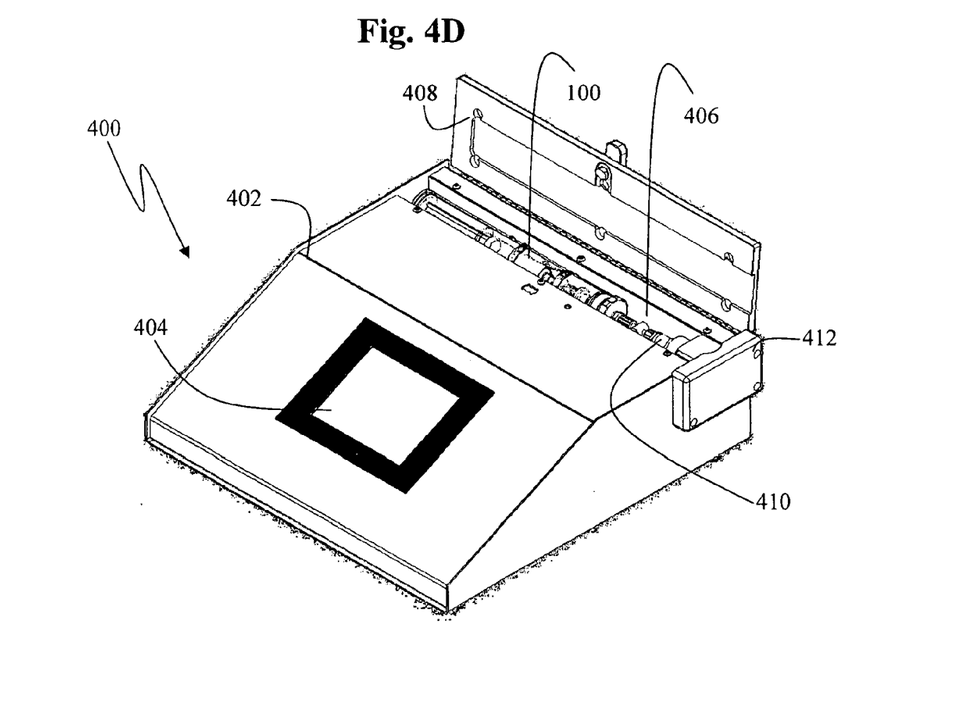
FIG. 4D is a perspective view of the exemplary ozone conversion unit having the exemplary syringe device received in a receptacle thereof.

Referring particularly to FIG. 3C-3E, after ozone is produce, sterility case 144 can be removed. The bottom open end of sterility case 144 can be uncoupled from sterility cap 136. Nevertheless, gas in gas chamber 108 can remain in a substantially sterile state, as would be expected. First stopcock valve 128 can be placed in the closed position and filter 132 can be uncoupled from first luer fitting 130 and a delivery device can be coupled to luer fitting 130. Filter 132 can be removed prior to injection so that the removed contaminants are not forced back into the patient during injection. A clinician in the non-sterile field can remove sterility case 144 and the clinician can couple syringe device 102 to a hypodermic needle. For example, a hypodermic needle can be coupled with luer fitting 130 for intradiscal injection of a substantially sterile dose of ozone gas by a clinician (e.g., doctor, nurse, etc.).

The disclosures of unpublished U.S. patent application Ser. No. 11/527,414 (Hooper), Ser. No. 11/727,978 (Hooper, et al.) and Ser. No. 11/976,362 entitled "SYSTEM FOR DELIVERING OZONE", "APPARATUS, METHOD AND SYSTEM FOR DELIVERING OXYGEN-OZONE" and "SYRINGE, SYSTEM AND METHOD FOR DELIVERING OXYGEN-OZONE", respectively, are incorporated by reference herein in their entireties. As will be recognized by one having ordinary skill in the art, a syringe devices in accordance with at least one embodiment of the present disclosure can be suitably designed to functionally replace exemplary sterile vials (i.e. oxygen-ozone cells) of the '414 application for use with exemplary ozone conversion units as otherwise disclosed (and further described herein below), with or without ordinary modification, in the '414 application. Alternatively, conventional ozone generators, with or without ordinary modification, can be used to convert a portion of oxygen gas to ozone gas within syringe devices in accordance with embodiments of the present disclosure.

There may not be a need to remove excess ozone from an ozone generator because the amount of ozone needed (without substantial excess) can be produced directly in an exemplary syringe device. An exemplary syringe device adapted for direct cooperation with a medical ozone generator can decrease manufacturing costs by combining the functionality of an ozone cell (e.g., sterile vial) with a therapeutic delivery instrument (e.g., a conventional syringe).

Moreover, syringe device embodiments can be suitably designed to functionally replace exemplary oxygen-ozone cells of the '978 application. Such embodiments can be filled with concentrated oxygen using exemplary apparatuses for concentrating oxygen from air as otherwise disclosed, with or without ordinary modification, in the '978 application. Alternatively, oxygen can be supplied to exemplary syringe devices by any other means known to one having ordinary skill in the art. As a couple non-limiting examples, medical grade oxygen can be supplied from supply tanks or hospital supply lines.

An exemplary ozone conversion unit may include an ozone UV measurement assembly, a data input mechanism such as a dial to allow the user to select a desired ozone concentration, and a data display to display input and output data such as desired concentrations and measurements. After a syringe device according to at least one exemplary embodiment is engaged to the ozone conversion unit, an ozone concentration may be selected and power applied to effect corona discharge and the resultant conversion of oxygen to the selected concentration of ozone. An exemplary syringe device may then be disengaged, thus allowing for therapeutic treatment. Embodiments may be employed in any of a variety of situations including, for example, the therapeutic treatment of humans or animals by way of injection.

The ozone conversion unit may be used to convert an amount of oxygen contained in an exemplary syringe device to ozone by facilitating power. Ozone conversion unit may include a high voltage transformer. In an exemplary embodiment, the high voltage transformer may have a potential difference of about 3-25 kV. The high voltage transformer may be connected to a power source and to another set of electrical contact points. In another exemplary embodiment, electrical contact points may be arranged to reversibly interface with the electrical contact points of an exemplary syringe device.

The ozone conversion unit may further include an input device (e.g., dial, keypad, touch screen, etc.), a UV measurement assembly and a data display. The UV measurement assembly may include components relating to measurements using UV absorption techniques, whereby a beam is passed through the ozone and oxygen mixture to be received by a detector. Such a beam may have a wavelength within a range on the UV spectrum known to those skilled in the art to be absorbed by ozone such as ranges UV-A, UV-B, and UV-C. In an exemplary embodiment, a beam having wavelengths of about 253.7 nm, within the bounds of the UV-C range, may be used. Also, in an exemplary embodiment, a mercury vapor lamp may be used to measure the concentration of ozone. An alternative exemplary embodiment may employ a UV light emitting diode or other instruments known to one having ordinary skill in UV absorption techniques. An exemplary detector may be a photodiode or other photo detecting instruments known to those having ordinary skill in the art. The dial may be used to regulate or input a desired ozone concentration. An exemplary therapeutically effective concentration of ozone is 6% or less by volume. An exemplary syringe device may be constructed to be received by the ozone conversion unit in such a way that orients an exemplary syringe device for successful UV measurement.

In an exemplary embodiment, the electrical contact points (e.g., conducting elements 148, 150) may be situated to interface with the interior of a receptacle formed in the ozone conversion unit that is capable of receiving an exemplary syringe device. The UV measurement assembly may be arranged to orient a UV measurement beam axially through and along the receptacle to be received by a UV detector. In an alternative embodiment, the UV measurement assembly may be arranged to orient the UV measurement beam through the receptacle transversely. A further exemplary embodiment may include a door to be closed upon or around an engaged exemplary syringe device, thereby reducing ambient light from infiltrating the receptacle and interfering with UV detector.

The data display may be used to display measurement data collected by a UV measurement assembly, indicate power status, or convey other relevant information such as input data or to confirm engagement of an exemplary syringe device within the ozone conversion unit and operating pressures. The data display may be used to display any information or data that may be useful to one having ordinary skill in the art. The ozone conversion unit may be constructed to receive power, which can be made to pass through the high voltage transformer, and both sets of electrical contact points, thereby causing the corona discharge assembly to act upon the oxygen contained by an exemplary syringe device and effect the selected concentration of ozone.

Optionally, the exemplary ozone conversion unit may also be constructed to detect nitrogen oxides (NOx). If an exemplary syringe device is contaminated with nitrogen, for example, due to ingress of air from such causes as a leak within the syringe device or improper functioning of a filling apparatus and system, then NOx will be produced by charging with the ozone conversion unit. Absorption techniques can be used to indirectly detect nitrogen ingress into the syringe device prior to charging. While nitrogen itself is optically transparent, $NO_x$ molecules, which will be created from the ionization of nitrogen and oxygen, absorb light at various frequencies between 227 and 550 nm. Many $NO_x$ bands overlap with that of ozone making it difficult to isolate these oxides. However, $NO_2$ has absorption bands (400-550 nm) that are distinct from ozone (253.7 nm) making it well suited to detect nitrogen ingress and formation of $NO_x$'s.

Also optionally, an exemplary ozone conversion unit or an exemplary syringe device may be constructed to measure leaks within the syringe device because at least one visual indicator or sensor for measuring changes in pressure known to those having ordinary skill in the art may be suitably placed for such a purpose. Moreover, the dielectric property of gases may provide another way to measure the amount of nitrogen potentially within the syringe device. Oxygen and nitrogen have different dialectic constants and may be detected based on this difference.

Referring to FIGS. 4A-4D, an exemplary ozone conversion unit is shown. Ozone conversion units consistent with the description above can be provided in various designs, as will be readily recognized by one having ordinary skill in the art. FIGS. 4A-4D show, inter alia, a design for an exemplary zone conversion unit in accordance with at least one exemplary embodiment.

Ozone conversion unit 400 can include housing 402 for housing components of ozone conversion unit 400. Housing 402 can frame data input and display mechanism 404. In at least one embodiment, data input and display mechanism 404 can be a touch screen. Data input and display mechanism 404 can allow a user to input a variety of data and view a variety of inputted and outputted data. For example, data input and display mechanism 404 can allow a user to select a desired ozone concentration. Moreover, data input and display mechanism 404 can be used to display measurement data collected by a UV measurement assembly, indicate power status, or convey other relevant information (e.g., input data, data confirming engagement of syringe device 100 within ozone conversion unit 400, operating pressures, etc.).

Ozone conversion unit 400 can include receptacle 406. Receptacle 406 can be accessed through the operation of lid 408. Within receptacle 406 can be holder 410. Holder 410 can be pivotally mounted within receptacle 406. Ozone conversion 400 can include guide 412 affixed to housing 402 proximate holder 410 for guiding and confirming that holder 410 is in an upright position. Syringe device 100 can be fitted on holder 410 and holder 410 can be pivoted to provide syringe device 100 within receptacle 406 for generating an amount of ozone gas from oxygen gas.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An ozone generation system, comprising:
   a syringe device having a syringe with a plunger slidably engaged with a barrel, the barrel and the plunger cooperating to define a gas chamber, the syringe enclosed by a sterility case;
   one or more electrodes attached to the syringe;
   one or more conducting elements on the sterility case, the one or more conducting elements directly or indirectly connected to the one or more electrodes; and
   an ozone conversion unit with a high voltage supply, the ozone conversion unit configured to interface with the syringe device, and the case maintains sterility of the syringe while passing a current from the one or more conducting elements to the one or more electrodes while interfaced with the ozone conversion unit to effectuate a corona discharge and produce an amount of ozone gas from an amount of oxygen gas within the gas chamber.

2. The ozone generation system of claim 1, further comprising:
   an apparatus for concentrating oxygen from ambient air having at least one zeolite chamber and a pump in fluid communication with the at least one zeolite chamber.

3. The ozone generation system of claim 2, wherein the ozone conversion unit and the apparatus for concentrating oxygen are provided within a shared housing having a single site for engaging the syringe device.

* * * * *